United States Patent [19]

Heiman

[11] Patent Number: 5,336,622
[45] Date of Patent: Aug. 9, 1994

[54] TRACERS FOR USE IN FLECAINIDE FLUORESCENCE POLARIZATION IMMUNOASSAY

[75] Inventor: Daniel F. Heiman, Libertyville, Ill.

[73] Assignee: Abbott Laboratories, Abbott Park, Ill.

[21] Appl. No.: 336,574

[22] Filed: Apr. 11, 1989

Related U.S. Application Data

[63] Continuation of Ser. No. 132,083, Dec. 11, 1987, abandoned, which is a continuation-in-part of Ser. No. 856,079, Apr. 25, 1986, abandoned.

[51] Int. Cl.⁵ .................. G01N 33/542; C07D 405/14
[52] U.S. Cl. .................................. 436/537; 436/546; 436/815; 544/209
[58] Field of Search ................ 544/209; 436/537, 800, 436/546, 805, 815

[56] References Cited

U.S. PATENT DOCUMENTS

| | | | |
|---|---|---|---|
| 3,900,481 | 8/1975 | Banitt et al. | 546/224 |
| 4,255,329 | 3/1981 | Ullman | 436/537 |
| 4,351,760 | 9/1982 | Khanna et al. | 436/546 |
| 4,420,568 | 12/1983 | Wang et al. | 436/546 |
| 4,476,228 | 10/1984 | Huchzermeier et al. | 436/546 |
| 4,476,229 | 10/1984 | Fino et al. | 436/546 |
| 4,481,136 | 11/1984 | Khanna et al. | 436/546 |
| 4,492,762 | 1/1985 | Wang et al. | 436/537 |
| 4,510,251 | 4/1985 | Kirkemo et al. | 436/546 |
| 4,585,862 | 4/1986 | Wang et al. | 436/537 |
| 4,588,697 | 5/1986 | Khanna et al. | 436/546 |
| 4,593,089 | 6/1986 | Wang et al. | 436/546 |
| 4,681,859 | 7/1987 | Kramer | 436/537 |

FOREIGN PATENT DOCUMENTS 2111476  7/1983  United Kingdom.

OTHER PUBLICATIONS

Colbert, et al., *Clin. Chem.*, 30(11):1765–1769 (1984).
Johnson, et al., *FEBS Letters*, 132(2):252–256 (Sep. 1981).
Shipchandler, et al., *Analytical Biochemistry*, 162:89–101 (1987).

*Primary Examiner*—Mary E. Ceperley
*Attorney, Agent, or Firm*—Gregory W. Steele; Daniel W. Collins

[57] ABSTRACT

A fluorescence polarization immunoassay for flecainide and tracers therefor are disclosed.

6 Claims, 10 Drawing Sheets

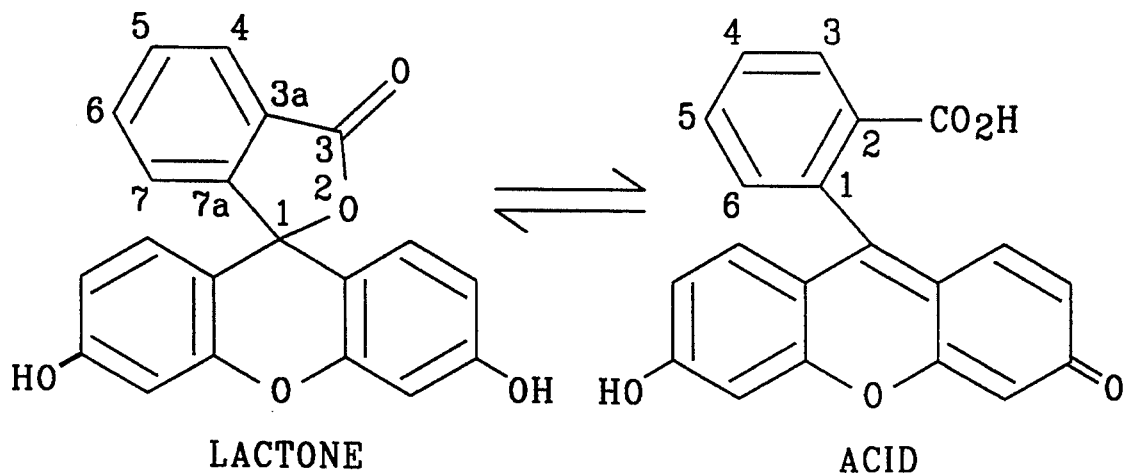
FIG. 3
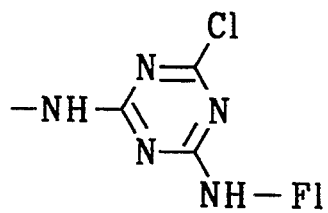
FIG. 4-1
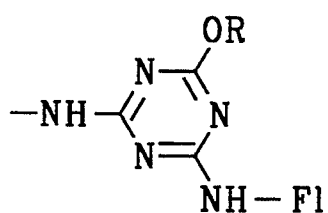
FIG. 4-2
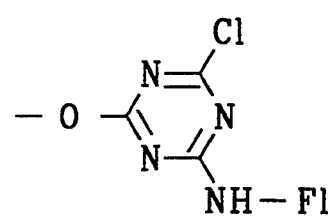
FIG. 4-3
—NH—CO—Fl
FIG. 4-4
—CO—NH—Fl
FIG. 4-5
—C(NH)—NH—Fl
FIG. 4-6
—NH—CO—NH—Fl
FIG. 4-7
—NH—CS—NH—Fl
FIG. 4-8
—O—CO—NH—Fl
FIG. 4-9
—O—CS—NH—Fl
FIG. 4-10
—SO$_2$—NH—Fl
FIG. 4-11
—O—CO—NH—SO$_2$—NHFl
FIG. 4-12

FIG. 11
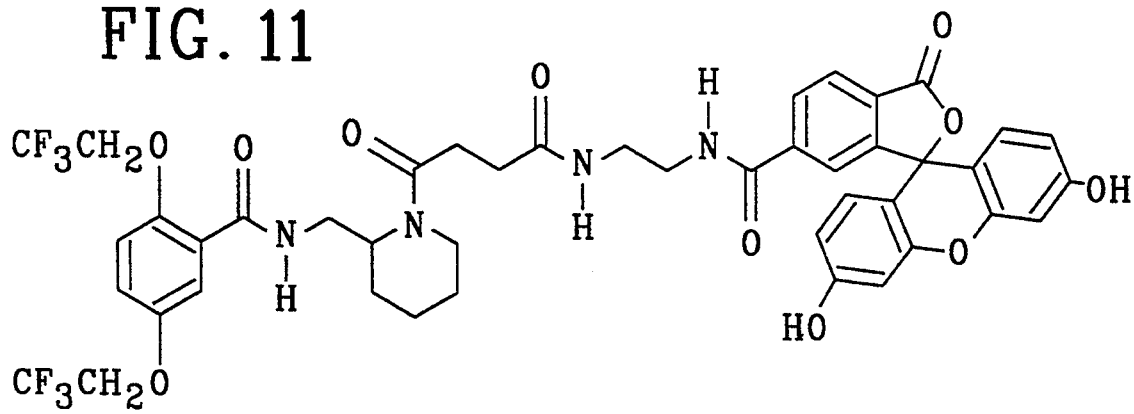
FIG. 12
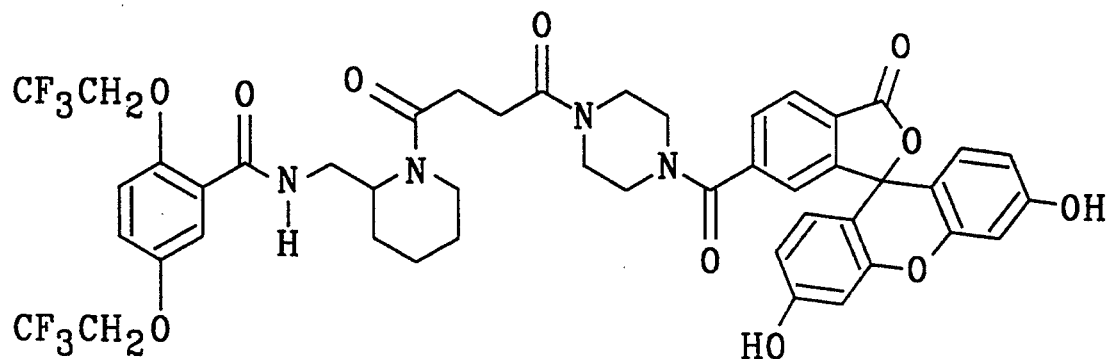
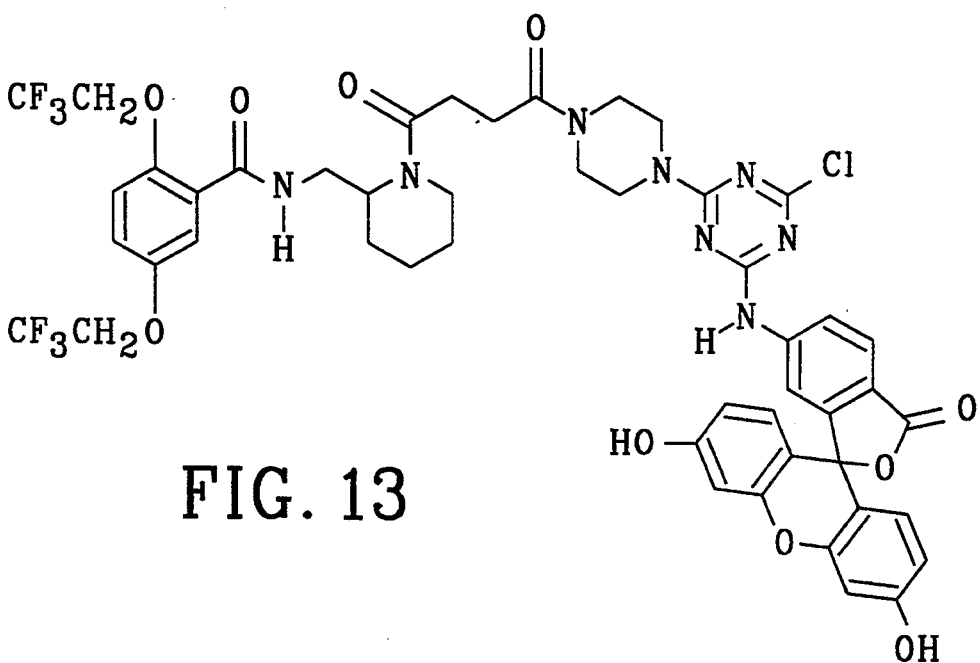
FIG. 13

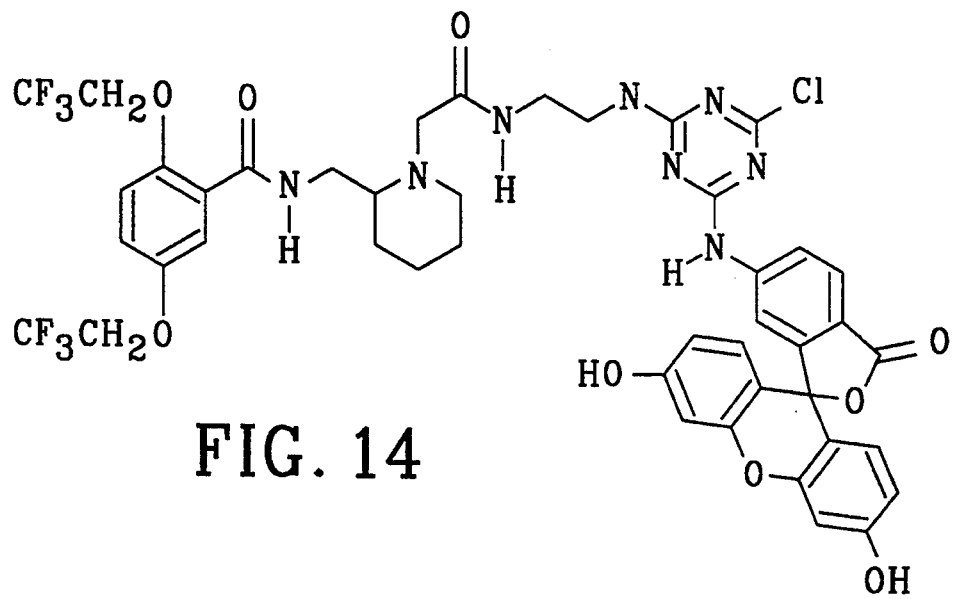
FIG. 14
FIG. 15
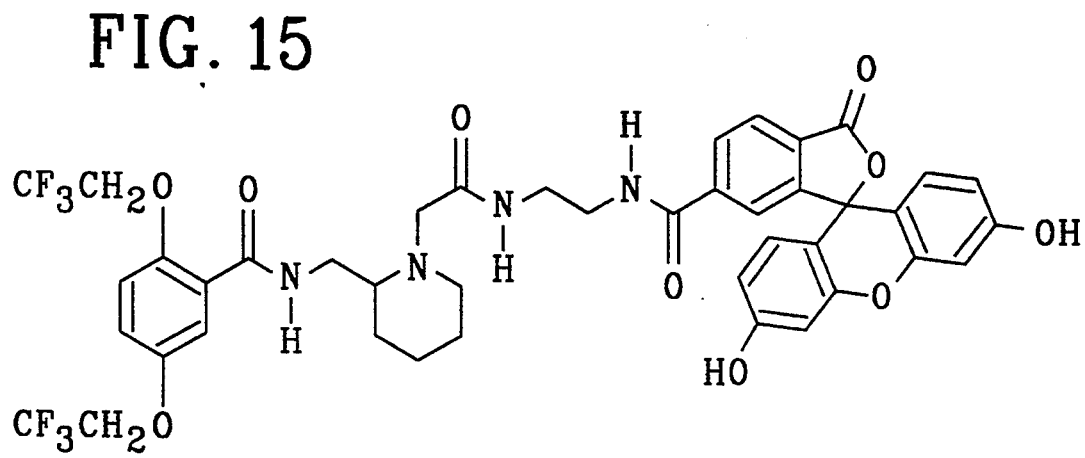
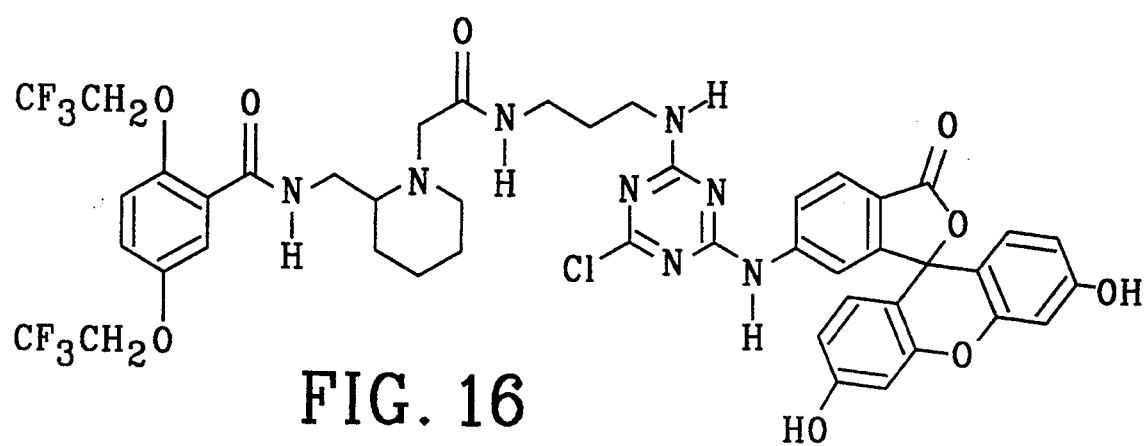
FIG. 16

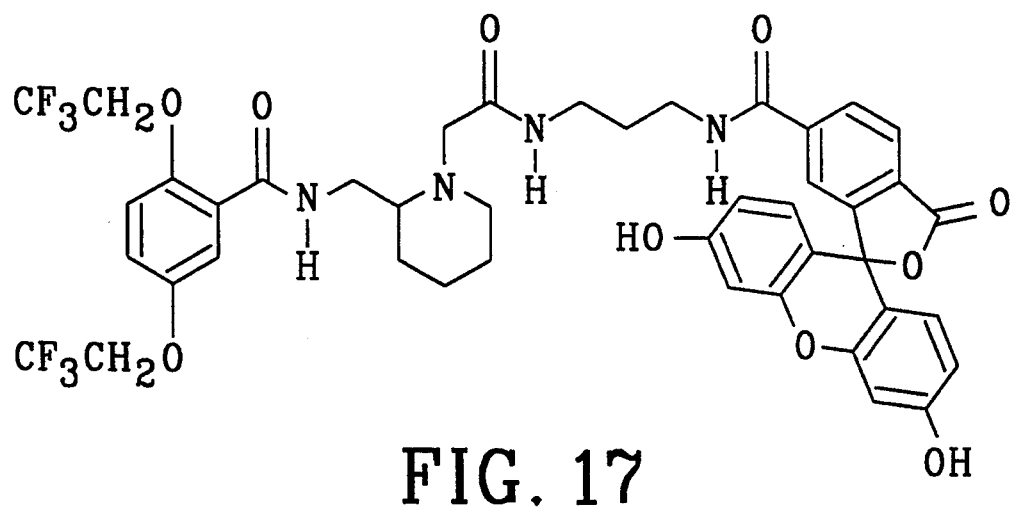
FIG. 17
FIG. 18
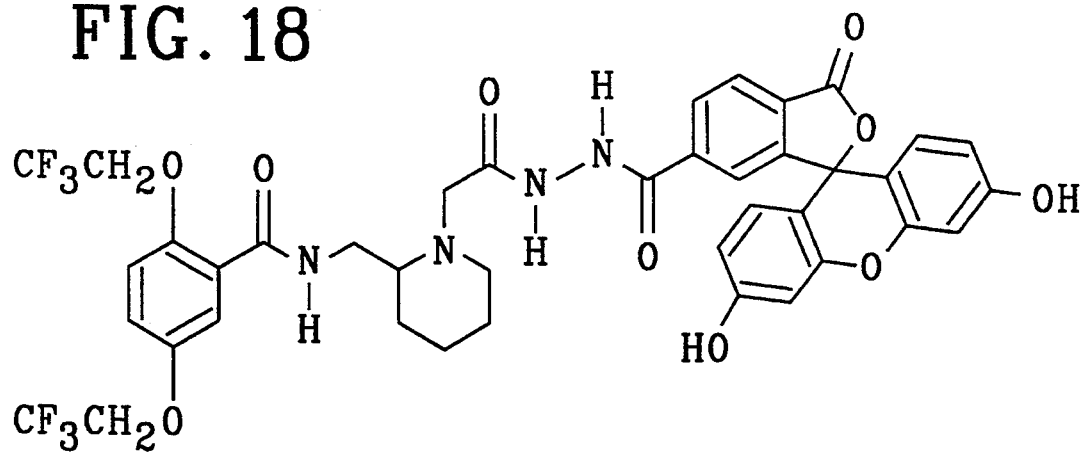
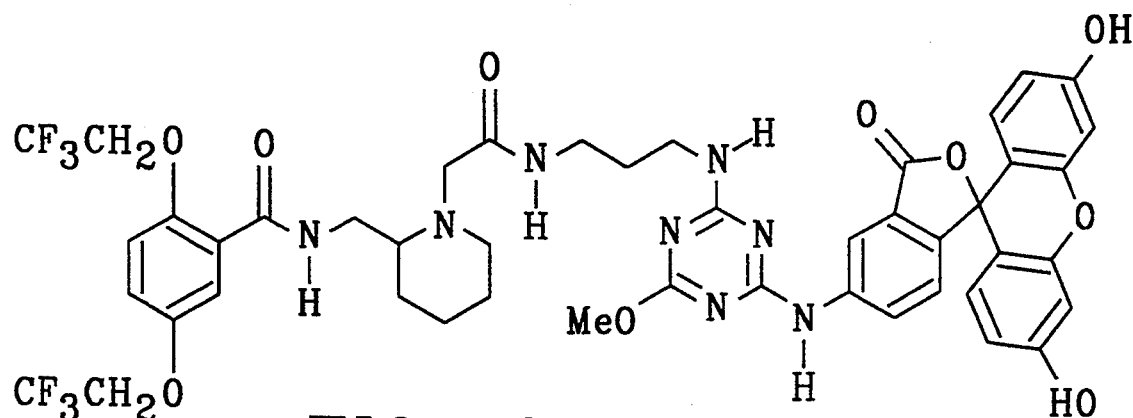
FIG. 19

FIG. 23
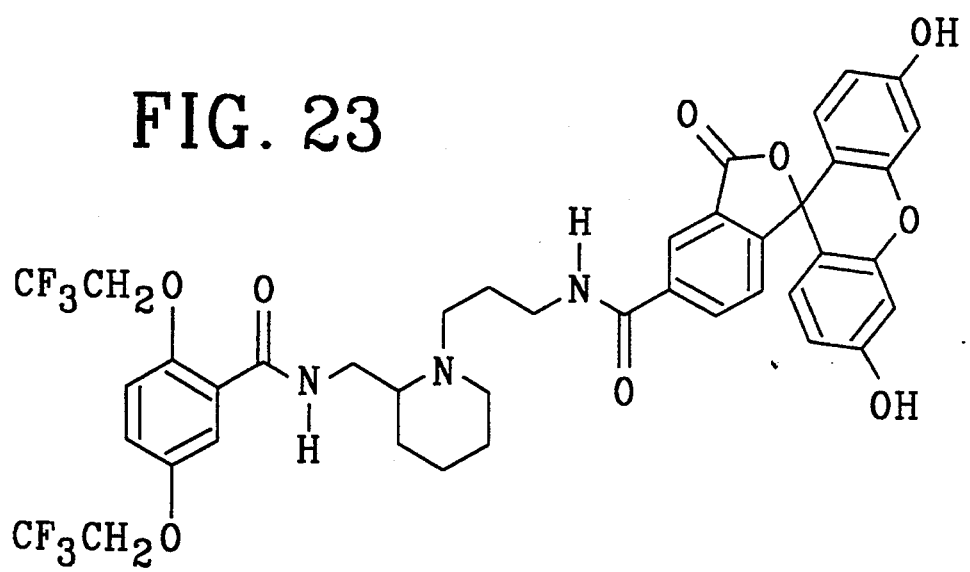
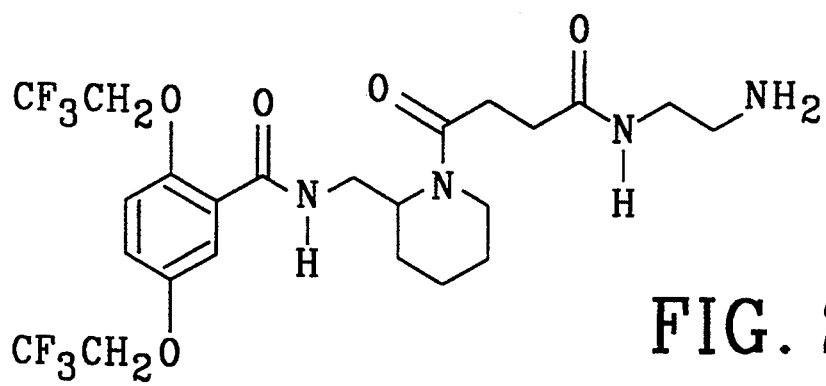
FIG. 24
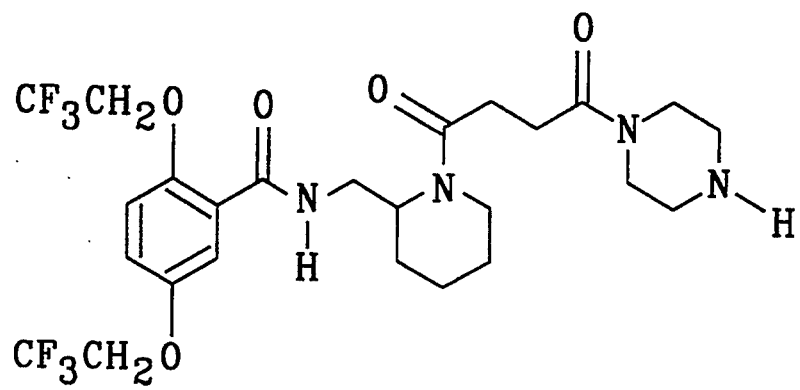
FIG. 25

TRACERS FOR USE IN FLECAINIDE FLUORESCENCE POLARIZATION IMMUNOASSAY

CROSS-REFERENCE TO RELATED APPLICATIONS

This is a continuation of U.S. Ser. No. 132,083, filed 11 Dec. 1987, abandoned, which is a continuation-in-part of U.S. Ser. No. 856,079, filed 25 Apr. 1986, abandoned.

BACKGROUND OF THE INVENTION

The present invention relates to a method and reagents for a fluorescence polarization immunoassay (FPIA) procedure for determining the amount of flecainide in fluids, especially biological fluids such as serum, plasma or urine, and to a method for making certain of the reagents. More specifically, the invention relates to (1) reagents for determining the amount of flecainide in a sample, viz., tracer and buffer solutions; (2) synthetic methods for preparing the tracer compounds; and (3) analytical methods for conducting the assay.

Flecainide acetate, or N-(2-piperidylmethyl)-2,5-bis (2,2,2-trifluoroethoxy)benzamide acetate, is a drug used to treat ventricular arrhythmias and tachycardia. Although flecainide acetate has been proven to be effective clinically, it can cause undesirable side effects if optimal dosage levels are exceeded. Therapeutic blood flecainide levels have been found to range from 0.2 to 1.0 microgram per milliliter, with 0.5 microgram per milliliter considered the mean effective concentration. Monitoring of serum flecainide levels combined with clinical data can provide the physician with useful information to aid in adjusting patient dosage, achieving optimal therapeutic effects while avoiding useless sub-therapeutic or harmful toxic dosage levels.

In the past, patient serum or plasma flecainide levels have typically been measured by high performance liquid chromatography (HPLC) or gas chromatography (GC). Although these methods are reasonably specific for detecting drug levels, they are not without drawbacks. They involve extensive sample preparation, time-consuming instrument set-up and a need for highly trained personnel.

In assays for other substances, competitive binding immunoassays have provided a more satisfactory alternative. Typically, competitive binding immunoassays are used for measuring ligands in a test sample. (For purposes of this disclosure, a "ligand" is a substance of biological interest to be determined quantitatively by a competitive binding immunoassay technique.) The ligands compete with a labeled reagent, or "ligand analog," or "tracer," for a limited number of receptor binding sites on antibodies specific to the ligand and ligand analog. The concentration of ligand in the sample determines the amount of ligand analog which binds to the antibody: the amount of ligand analog that will bind is inversely proportional to the concentration of ligand in the sample, because the ligand and the ligand analog each bind to the antibody in proportion to their respective concentrations.

Fluorescence polarization provides a quantitative means for measuring the amount of tracer-antibody conjugate produced in a competitive binding immunoassay. Fluorescence polarization techniques are based on the principle that a fluorescent labeled compound, when excited by plane polarized light, will emit fluorescence having a degree of polarization inversely related to its rate of rotation. Accordingly, when a tracer-antibody conjugate having a fluorescent label is excited with plane polarized light, the emitted light remains highly polarized because the fluorophore is constrained from rotating between the time that light is absorbed and emitted. In contrast, when an unbound tracer is excited by plane polarized light, its rotation is much faster than that of the corresponding tracer-antibody conjugate. As a result, the light emitted from the unbound tracer molecules is depolarized.

Fluorescence polarization immunoassay techniques are well known in the art, to date, however, the use of such techniques for the determination of flecainide levels have not been successfully attempted. Thus, the present invention offers an advance in the art in that highly sensitive tracers, a method for making the tracers, and an assay using the tracers are provided specifically for the determination of flecainide. The assay conducted in accordance with the present invention is particularly accurate, as will be explained infra.

SUMMARY OF THE INVENTION

The present invention is directed to an FPIA for flecainide; to tracers for use in the assay; and to methods for making such tracers.

A first aspect of the invention relates to the discovery of unique tracers having novel structures. According to this first aspect of the invention, the tracers can be represented by the structural formula shown in FIG. 2 of the drawings, wherein:

R is a halo-substituted triazinyl group; and
X is selected from (—CH$_2$)$_3$NH— or

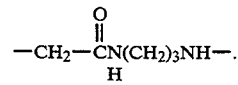

According to another aspect of the invention, a process for measuring concentration of flecainide is provided. A sample is contacted with flecainide antiserum, and with a fluorescein flecainide conjugate of FIG. 2. Plane-polarized light is then passed through the solution to obtain a fluorescence polarization response, and this response is detected as a measure of the amount of flecainide in the sample.

Further objects and attendant advantages of the invention will be best understood from a reading of the following detailed description taken together with the Figures and the Examples.

BRIEF DESCRIPTION OF THE DRAWINGS

In the following Figures, the symbol "F1" represents a fluorescein moiety, and the various other Symbols are noted in the Detailed Description.

FIG. 3 shows the alternate structural formulae and names of the fluorescein moiety included in the tracers of the present invention.

FIGS. 4-1 through 4-12 show various linkages that couple the fluorescein moiety to a flecainide precursor; F1 designates fluorescein.

FIG. 4-1 is the radical 3-chloro-5-(fluoresceinylamino)triazin-1-ylamino-.

FIG. 4-2 is the radical 3-hydroxy-5-(fluoresceinylamino)triazin-1-ylamino-.

FIG. 4-3 is the radical 3-chloro-5-(fluoresceinylamino)triazin-1-yloxy-.

FIG. 4-4 is the radical fluoresceinylcarbonylamino-.

FIG. 4-5 is the radical fluoresceinylaminocarbonyl-.

FIG. 4-6 is the radical fluoresceinylcarbonimido-.

FIG. 4-7 is the radical fluoresceinylaminocarbonylamino-.

FIG. 4-8 is the radical fluoresceinylaminothiocarbonylamino-.

FIG. 4-9 is the radical fluoresceinylaminocarbonyloxy-.

FIG. 4-10 is the radical fluroesceinylaminothiocarbonyloxy-.

FIG. 4-11 is the radical fluoresceinylaminosulfonyl-.

FIG. 4-12 is the radical fluoresceinylaminosulfonylaminocarbonyloxy-.

FIGS. 5 through 24 show various examples of flecainide tracers.

FIGS. 25 through 29 show various intermediates useful in making flecainide tracers.

DETAILED DESCRIPTION OF THE INVENTION

Figure 1:
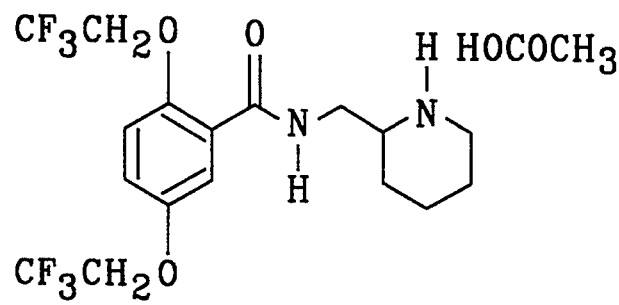
FIG. 1 shows the general structure of the drug flecainide acetate to be quantitatively determined in accordance with the present invention.

The various aspects of the invention will now be discussed in detail in relation to the Figures.

Definitions and Explanatory Material

The present invention involves the use of fluorescein and derivatives of fluorescein. In particular, a necessary property of fluorescein and its derivatives for the usefulness of the tracer compounds is the fluorescence of fluorescein. Fluorescein exists in two tautomeric forms, illustrated in FIG. 3, depending on the acid concentration (pH) of the environment. In the open (acid) form, there are a number of conjugated double bonds which make that form of fluorescein (and compounds containing a fluorescein moiety) capable of absorbing blue light and emitting green fluorescence after an excited state lifetime of about four nanoseconds. When the open and closed forms coexist, the relative concentration of molecules in the open and closed forms is easily altered by adjustment of the pH level. Generally, the tracer compounds of the present invention exist in solution as biologically acceptable salts such as sodium, potassium, ammonium and the like, allowing the compounds to exist in their open, fluorescent form when employed in the analytical methods of the present invention. The specific salt present will depend on the buffer employed to adjust the pH level. For example, in the presence of a sodium phosphate buffer, the compounds in the present invention will generally exist in the open form, as a sodium salt.

As used herein, the term "fluorescein", either as an individual compound or as a component of a larger compound, is meant to include both the open and closed forms, if they exist for a particular molecule, except in the context of fluorescence. An open form is necessary for the fluorescence to occur.

A tracer in solution which is not complexed to an antibody is free to rotate in less than the time required for absorption and re-emission of fluorescent light. As a result, the re-emitted light is relatively randomly oriented so that the fluorescence polarization of a tracer not complexed to an antibody is low, approaching zero. Upon complexing with a specific antibody, the tracer-antibody complex thus formed assumes the rotation of the antibody molecule, which is slower than that of the relatively small tracer molecule, thereby increasing the polarization observed. Therefore, when a ligand competes with the tracer for antibody sites, the observed polarization of fluorescence of the resulting mixture of the free tracer and tracer-antibody complex assumes a value intermediate between that of the tracer and that of the tracer-antibody complex. If a sample contains a high concentration of the ligand, the observed polarization value is closer to that of the free ligand, i.e., low. If the test sample contains a low concentration of the ligand, the polarization value is closer to that of the bound ligand, i.e., high. By sequentially exciting the reaction mixture of an immunoassay with vertically and then horizontally polarized light and analyzing only the vertically polarized component of the emitted light, the polarization of fluorescence in the reaction mixture may be accurately determined. The precise relationship between polarization and concentration of the ligand to be determined may conveniently be established by measuring the polarization values of calibrators with known concentrations. The concentration of the ligand can be interpolated from a standard curve prepared in this manner.

The particular tracers formed in accordance with this invention have been found to produce very good assays, as discussed infra.

The Reagents

The objective in designing a competitive binding immunoassay for flecainide is to set up a reasonably balanced competition between the drug flecainide and the tracer for the recognition sites on the antibody. Widely varying structures for haptens and tracers may be successful in achieving this goal. For the purposes of this invention, "haptens" are precursors of the immunogens, comprising generally a substituted flecainide derivative bearing a group suitable for linking to an immunologically active carrier.

The Antibodies

The antibodies employed in the present invention are prepared by eliciting a response in rabbits or sheep to appropriate immunogens. The immunogen is administered to animals or to in vitro cultures of immunocompetent cells by a series of innoculations, in a manner well known to those skilled in the art. It should be understood that although sheep were the preferred immune host to flecainide immunogens in the experiments detailed herein, any in vitro or in vivo host capable of producing antibodies may be employed.

The Structure of the Tracers

Figure 2:
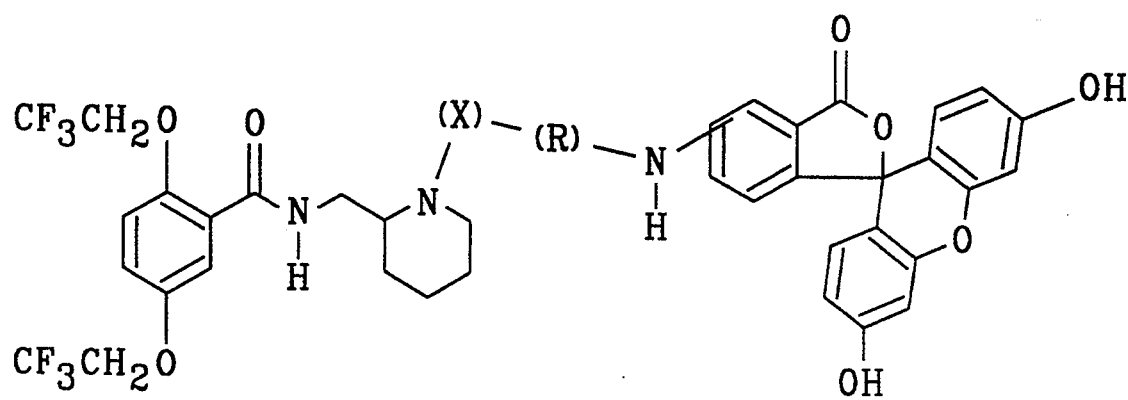
FIG. 2 shows a general structural formula for the tracers of the present invention, as well as the classes of reactants used in preparing them.

The tracers of the present invention can be represented by the general structural formula shown in FIG. 2 where R is a halo-substituted triazinyl, and X is selected from —(CH$_2$)$_3$NH— or

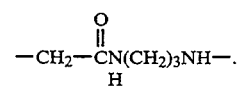

Figure 5:
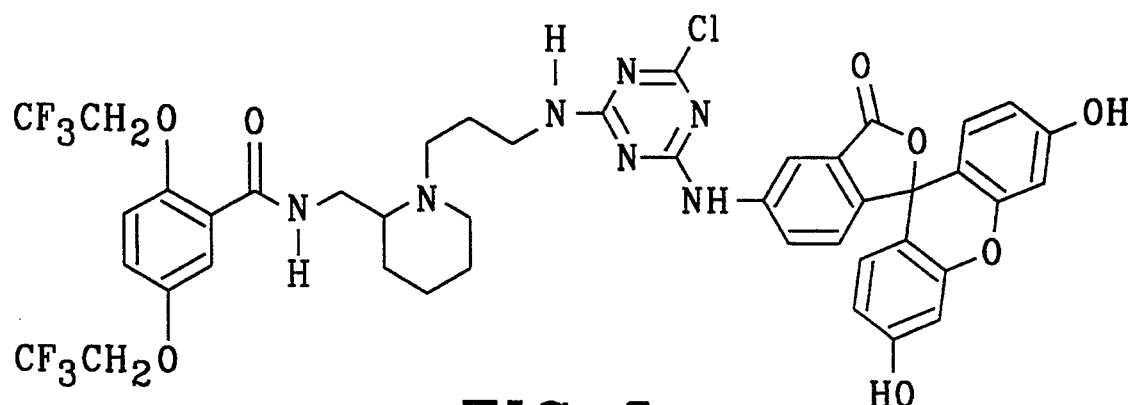
Figure 21:
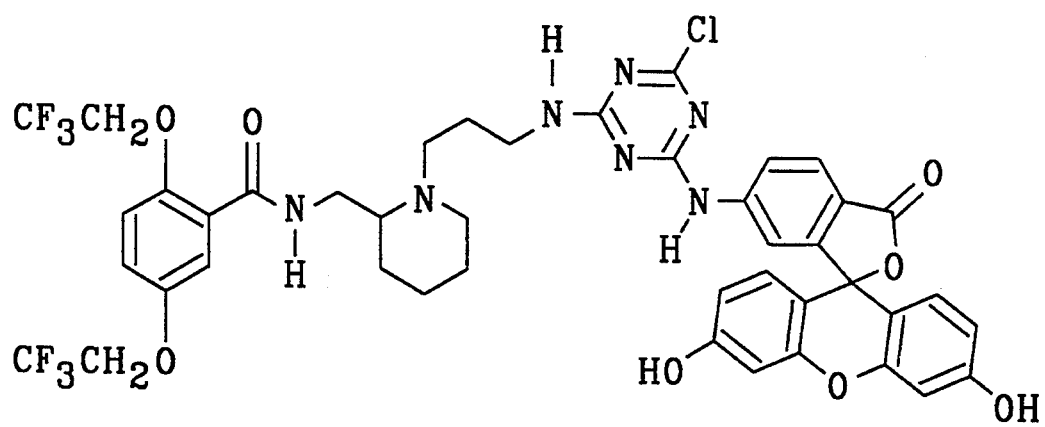

In a preferred form of the invention, the tracer has the structural formula shown in FIG. 5. Other embodiments of this invention are shown in FIGS. 16 and 21.

For comparison with the tracers of this invention, various other tracers have been tested, for example, flecainide derivatives linked to a fluorescein derivative by, for example, an amido, amidino, triazinylamino, carbamido, thiocarbamido, carbamoyl, sulfonamido, or sulfonylcarbamoyl group, as shown in FIG. 4. The tracers of this invention and those tested for comparison were prepared by linking the appropriate fluorescein derivative to a flecainide derivative containing an amino, carboxylic acid, sulfonic acid, hydroxy, imidate, hydrazide, isocyanate, chloroformate, chlorosulfonylcarbamoyl, or like group, as will be discussed in the context of the synthetic method and the Examples below.

By way of example, many of the following fluorescein derivatives were synthesized:

| | |
|---|---|
| Fl—NH$_2$ | fluorescein amine |
| Fl—CO$_2$H | carboxyfluorescein |
| Fl—NHCOCH$_2$I | α-iodacetamidofluorescein |
| Fl—NHCOCH$_2$Br | α-bromoacetamidofluorescein |
| Fl—NH—(triazine with 2 Cl) | 2,4-dichloro-1,3,5-triazin-2-ylamino-fluorescein (DTAF) |
| Fl—NH—(triazine with OCH$_3$ and Cl) | 4-chloro-6-methoxy-1,3,5-triazin-2-ylamino-fluorescein |

The Synthesis of the Tracers

Figure 2A:
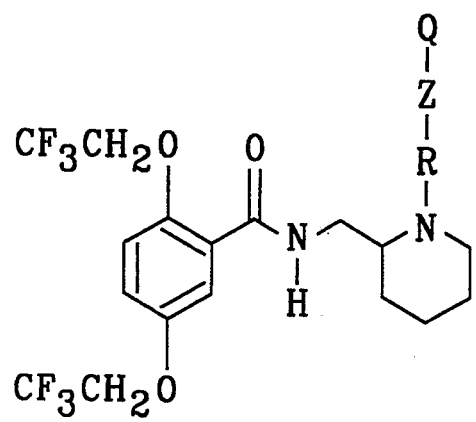
FIG. 2A shows a general structure for other classes of tracers for comparison with the tracers of this invention.

Tracers are made by coupling a fluorescein moiety or a derivative of fluorescein, to the general structure shown in FIG. 2A wherein Q is hydrogen, hydroxyl or a leaving group; Z is NH, S, O, C=O, SO$_2$ or C=NH and R is a linking group including up to 10 heteroatoms and having a total of from 0 to 20 carbon and heteroatoms; arranged as a straight or branched chain and containing up to two ring structures. The fluorescein moiety can be linked to the amino, carboxyl, imidate or alkoxy functional group by an amide, an amidine, a urea, a carbamate, a sulfonamide, a triazinylamino or a sulfonylcarbamate linkage, as shown in FIG. 4. In the preferred embodiment of this invention (FIG. 5), the fluorescein derivative is dichlorotriazinylamino-fluorescein (DTAF) (Isomer I), available from Research Organics, Cleveland, Ohio, and this is coupled to a precursor shown in FIG. 2A (wherein R=(CH$_2$)$_3$, Z=NH and Q=H).

The DTAF is coupled to the aminoalkyl derivative of flecainide by stirring the two compounds in methanol between a temperature of about 0° C. and the boiling point of the solvent. Basic compounds such as triethylamine may be added if desired, and especially if a salt (such as the hydrochloride or acetate) of the amine precursor is employed in the reaction. Other solvents, such as dimethylformamide or dimethylsulfoxide, may be used. Usable tracers can be prepared from a variety of flecainide derivatives.

All flecainide derivatives that have a terminal amino group, such as amino, hydrazinyl, hydrazido or the like, are coupled to carboxyfluorescein by the active ester method or the mixed anhydride method and coupled to the DTAF or alkoxy chlorotriazinylaminofluorescein by simply mixing the two materials in solution. The amino group can be converted to the isocyanate group by reaction with phosgene. This is then condensed with aminofluorescein to produce the tracer.

Flecainide derivatives having a terminal mercapto group are coupled in an inert solvent with α-bromoacetamidofluorescein or α-iodoacetamido-fluorescein.

All flecainide derivatives that have a terminal carboxylic acid group, such as carboxylic acid, (aminohydroxyl)alkylcarboxylic acid or the like, are coupled to aminofluorescein by the active ester method or mixed anhydride methods.

All flecainide derivatives that have a terminal hydroxy group can be coupled to fluorescein by reaction with DTAF, α-iodoacetamidofluorescein or α-bromoacetamidofluorescein in solution. The hydroxy group can be converted to the chlorosulfonylcarbamoyl or chloroformate groups by reaction with chlorosulfonylisocyanate or phosgene, respectively. These derivatives are then coupled to aminofluorescein in solution to produce the tracer.

Sulfonic acid derivatives of flecainide are converted to the corresponding sulfonyl chlorides by reaction with a chlorinating reagent such as thionyl chloride, phosphoryl chloride, phosphorus pentachloride, or the like. The sulfonyl halides are then reacted with aminofluoresceins or other fluorescein derivatives bearing reactive amino groups, usually in the presence of an added basic compound, to give the tracers.

Flecainide derivatives that have a terminal nitrile group are converted to imidates in anhydrous alcohol in the presence of hydrogen chloride gas. The imidate is then coupled to fluorescein amine in solution to prepare the tracer.

The Assay

The tracers of the present invention have been found to measure levels of flecainide accurately and specifically in serum and plasma. FIG. 1 shows the structure of the drug flecainide that can be quantitatively determined in accordance with the present invention. The assay of the present invention provides a more rapid and convenient flecainide assay method than prior art methods, because it requires no specimen treatment before analysis, the reagents are chemically and thermally stable, the assay system has minimal cross-reactivity to flecainide-like compounds and, because of its simplicity, may be carried out rapidly on highly automated equipment.

In accordance with the analytical methods of the present invention, i.e., the methods of determining flecainide by a fluorescence immunoassay procedure using the tracer compounds of the invention, a sample containing or suspected of containing flecainide is intermixed with a biologically acceptable salt of a tracer and an antibody specific to flecainide and the tracer. The flecainide and tracer compete for a limited number of antibody sites, resulting in the formation of complexes. Because the concentration of tracer and antibody is maintained constant, the ratio of flecainide antibody complex to tracer-antibody complex formed is directly proportional to the amount of flecainide in the sample. Therefore, upon exciting the mixture with linearly polarized light and measuring the polarization of the fluorescence emitted by a tracer and a tracer-antibody complex, one is able to determine quantitatively the amount of flecainide in the sample.

The results can be quantified in terms of net millipolarization units, span (in millipolarization units) and relative intensity. The measurement of millipolarization units indicates the maximum polarization when a maximum amount of the tracer is bound to the antibody in the absence of any flecainide. The higher the net millipolarization units, the better the binding of the tracer to the antibody. The span is an indication of the difference between the net millipolarization at the points of maximum and minimum amount of tracer bound to the antibody. A larger span provides for a better numerical analysis of data. The intensity is a measure of the strength of the signal above background. Thus, a higher intensity is determined at about 0.5 to 2.0 nanomolar for the preferred tracers of the invention, as the sum of the vertically polarized intensity plus twice the horizontally polarized intensity. The intensity of the tracer signal can range from about three times to about thirty times the background noise, depending upon the concentration of the tracer and other assay variables. For the purposes of the present invention, an intensity of at least five times that of background noise is preferred.

Table I shows the results obtained with various embodiments of the present invention compared with other possible flecainide tracers, in terms of span, millipolarization units and intensity. In all instances, the antiserum employed was raised in sheep. As can be seen from this data, an assay produced by use of the tracer of FIG. 5 provides excellent results and is presently the most preferred. In addition, the tracers represented by FIGS. 16 and 21 also produced acceptable results and thus are alternative preferred tracers.

TABLE I

Figure 6:
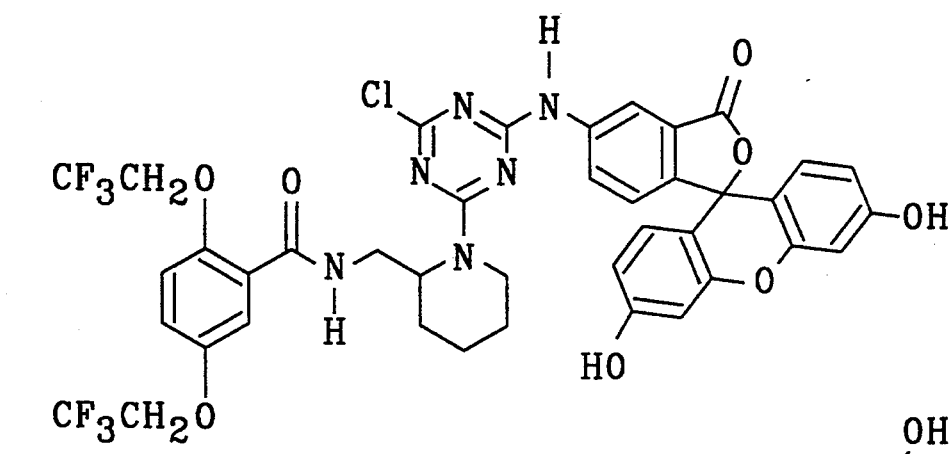
Figure 7:
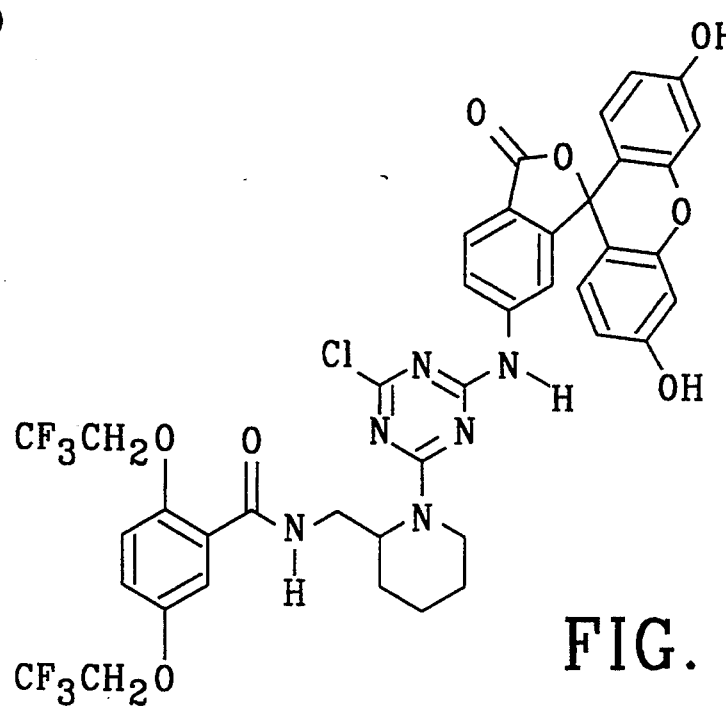
Figure 8:
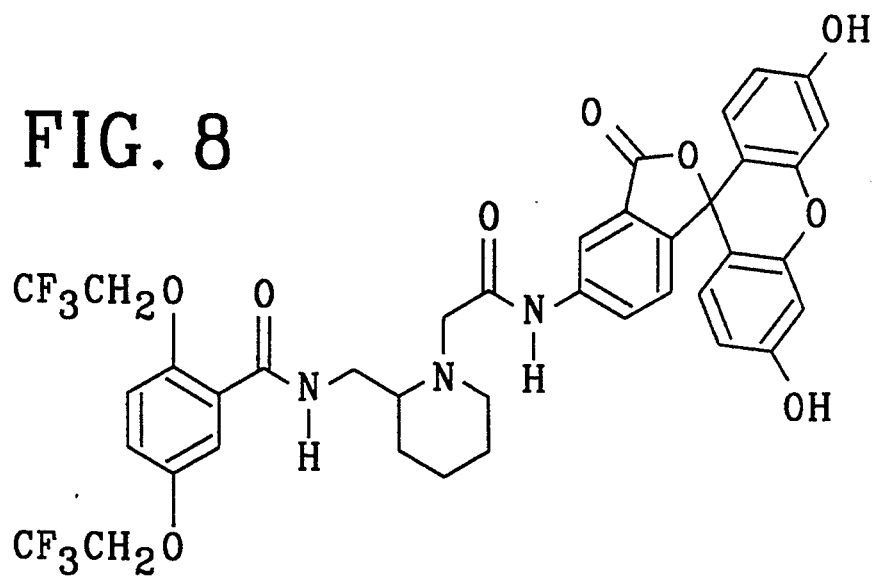
Figure 9:
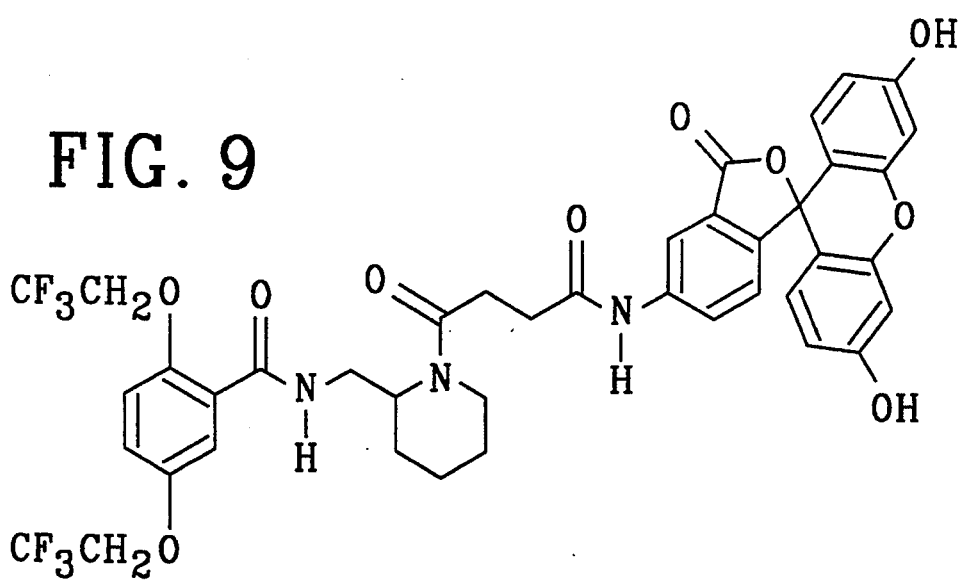
Figure 10:
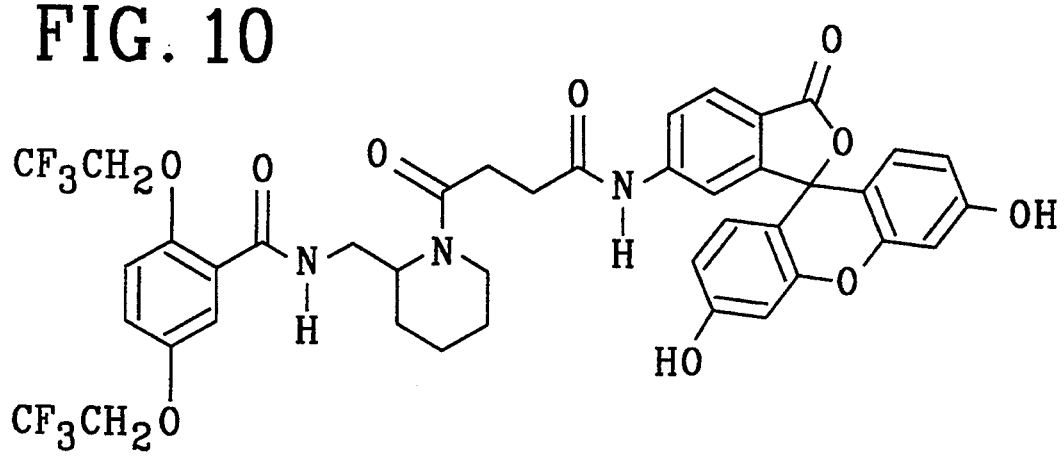
Figure 20:
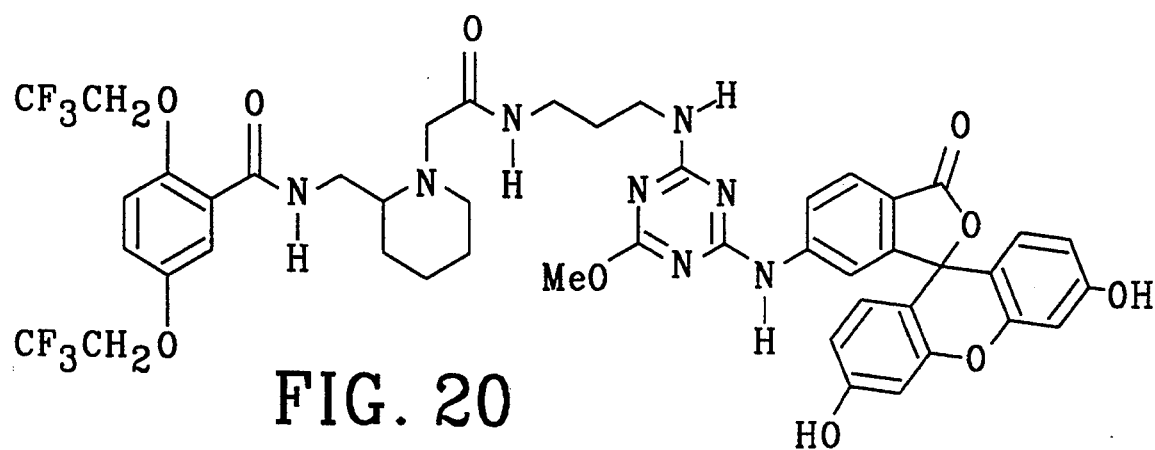
Figure 22:
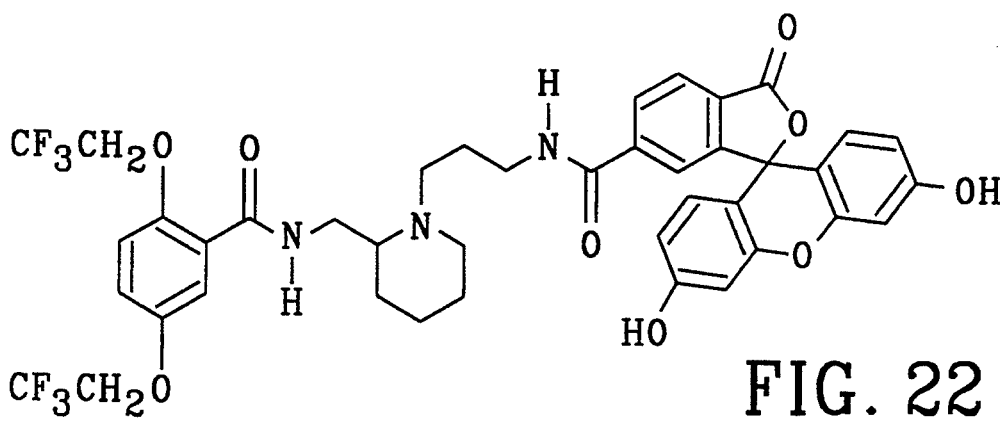

| Tracer | Net Polarization* | Span* | Intensity** |
|---|---|---|---|
| FIG. 5 | 217 | 110 | 5.9 |
| FIG. 6 | 240 | 60 | 4.5 |
| FIG. 7 | 322 | 77 | 6.4 |
| FIG. 8 | 189 | 39 | 8.1 |
| FIG. 9 | 198 | 49 | 7.7 |
| FIG. 10 | 220 | 86 | 9.1 |
| FIG. 11 | 240 | 86 | 13.0 |
| FIG. 12 | 217 | 83 | 7.8 |
| FIG. 13 | 303 | 84 | 6.2 |
| FIG. 14 | 223 | 62 | 5.5 |
| FIG. 15 | 233 | 89 | 10.0 |
| FIG. 16 | 289 | 104 | 19.0 |
| FIG. 17 | 199 | 69 | 10.4 |
| FIG. 18 | 212 | 65 | 7.0 |
| FIG. 19 | 274 | 72 | 2.94 |
| FIG. 20 | 285 | 79 | 4.8 |
| FIG. 21 | 273 | 104 | 7.8 |
| FIG. 22 | 216 | 69 | 11.6 |
| FIG. 23 | 214 | 74 | 6.8 |

*In millipolarization units
**Expressed as the ratio of net intensity to background noise.

The pH at which the method of the present invention is practiced must be sufficient to allow the fluorescein moiety of the tracers to exist in their open form. The pH may range from about 3 to 12, more preferably in the range of from about 5 to 10, and most desirably from about 6 to 9. Various buffers may be used to achieve and maintain the pH during the assay procedure. Representative buffers include borate, citrate, acetate, phosphate, carbonate, tris, barbital and the like. The particular buffer employed is not critical to the present invention, but the tris and phosphate buffers are preferred. The cation portion of the buffer will generally determine the cation portion of the tracer salt in solution.

The preferred method of the improved assay of the present invention will now be discussed in detail. The assay is a "homogenous assay", which means that the end polarization readings are taken from a solution in which bound tracer is not separated from unbound tracer. This represents a distinct advantage over heterogenous immunoassay procedures wherein the bound tracer must be separated from the unbound tracer before a reading can be taken.

The reagents for the fluorescence polarization assay of the present invention comprise antibody specific for flecainide and tracer. Additionally, largely conventional solutions including a flecainide pretreatment solution, a dilution buffer, flecainide calibrators and flecainide controls are desirably prepared. Typical solutions of these reagents, some of which are described herein, are commercially available in assay "kits" from Abbott Laboratories, Abbott Park, Ill.

All percentages expressed herein are weight/volume unless otherwise indicated. The tracer formulation presently preferred is 82 nanomolar tracer in: 0.1 molar tris buffer at pH 5.5; 5% 5-sulfosalicylate; and 0.1% sodium azide. The antiserum formulation comprises sheep antiserum diluted with: 1% normal sheep serum (volume/volume); and 0.1% sodium azide. The silution buffer comprises: 0.1 molar sodium phosphate at pH 7.5; 0.1% sodium azide; and 0.01% bovine gamma globulin. The pretreatment formulation comprises: 0.1 molar tris buffer at pH 5.5; 5% 5-sulfosalicylate; and 0.1% sodium azide. Calibrators comprising flecainide in normal human serum at concentrations of 0.0, 0.1, 0.25, 0.50, 1.0 and 1.5 milligrams per liter, with 0.1% sodium azide preservative are useful. Controls comprising flecainide in normal human serum are provided at concentrations of 0.15, 0.60 and 1.20 milligrams per liter with 0.1% sodium azide as a preservative.

The preferred procedure is especially designed to be used in conjunction with the Abbott TDx® polarization analyzer available from Abbott Laboratories, Irving, Tex. 50 microliters of serum or plasma are required. The calibrators, controls, or unknown samples are pipetted directly into the sample well of the TDx® sample cartridge. One of the advantages of this procedure is that the sample does not require any special preparation. If a TDx® flecainide assay kit is being used with the TDx® analyzer, samples are placed directly into a sample carousel, the caps from each of the three reagent containers in the kit are removed and placed into designated wells inside the TDx® analyzer, and the assay procedure from this point is fully automated.

If a manual assay is being performed, the sample is mixed with the pretreatment solution in dilution buffer and a background reading is taken. The tracer is then mixed with the assay. The antibody is then finally mixed into the test solution. After incubation, a fluorescence polarization reading is taken.

The fluorescence polarization value of each calibrator, control or sample is determined and may be printed on the output tape of an instrument such as the Abbott TDx® polarization analyzer. A standard curve is generated in the instrument by plotting the polarization of each calibrator versus its concentration using nonlinear regression analysis. The concentration of each control or sample is read off the stored calibration curve and printed on the output tape.

With respect to the foregoing preferred procedure, it should be noted that the tracer, antibody, pretreatment solution, calibrators and controls should be stored between about 2° and about 8° C., while the dilution buffer should be stored at ambient temperature. A standard curve and controls should be run every two weeks, with each calibrator and control run in duplicate. Controls should be run daily and all samples can be run in replicates if so desired.

It should be understood that the foregoing Detailed Description and the following Examples are intended to be illustrative, but not limiting, with respect to the scope of the present invention. Various modifications will become apparent to one skilled in the art, and thus it is intended that the scope of the invention be defined solely by the claims and legal equivalents thereof.

EXAMPLES

Examples 1 through 19 describe experiments that were performed with the present invention.

EXAMPLE 1

Preparation of the Tracer of FIG. 6

Flecainide acetate (9.5 mg) and 2-(fluorescein-5-yl)amino-4,6-dichloro-1,3,5-triazine (8.5 mg) were dissolved in 0.15 ml of methanol and stirred at ambient temperature for 3½ hours. The reaction mixture was streaked directly onto a thin-layer silica gel plate and chromatographed with chloroform/methanol to give the tracer.

EXAMPLE 2

Preparation of the Tracer of FIG. 7

Flecainide acetate (9.5 mg) and 2-(fluorescein-6-yl)amino-4,6-dichloro-1,3,5-triazine (8.0 mg) were taken up on 0.15 ml of methanol and stirred at ambient temperature for 16 hours. The reaction mixture was streaked onto a thin-layer silica gel place and chromatographed with chloroform/methanol to give the tracer.

EXAMPLE 3

Preparation of the Tracer of FIG. 8

Flecainide acetate (23.7 mg), 5-bromoacetamidofluorescein (15.6 mg) and triethylamine (0.0116 ml) were dissolved in 0.25 ml of methanol and stirred at ambient temperature for 48 hours. The product was isolate by chromatography on a thin layer silica gel plate developed with chloroform-methanol.

EXAMPLE 4

Preparation of the Tracer of FIG. 9

Flecainide hemisuccinamide (25.7 mg), triethylamine (0.0066 ml) and isobutyl chloroformate (6.8 mg) were dissolved in 0.4 ml of dimethylformamide chilled in an ice bath and stirred for 1 hour. The solution of activated precursor was divided in two, 5-aminofluorescein (8.7 mg) was added to one portion, the mixture was allowed to warm to ambient temperature and stirring was continued for 14 hours. The solvent was removed and the residue was chromatographed on thin layer silica gel plates with chloroform-methanol and again with benzene-ethyl acetate-acetone to give the pure tracer.

EXAMPLE 5

Preparation of the Tracer of FIG. 10

One half of the solution of activated precursor prepared in Example 4 was stirred at ambient temperature with 8.7 mg of 6-aminofluorescein for 15 hours. The dimethylformamide was removed in vacuo, and the residue was chromatographed on thin layer silica gel plates with chloroform-methanol and again with benzene-ethyl acetate-acetone to give the pure tracer.

EXAMPLE 6

Preparation of the Tracer of FIG. 11

The precursor of FIG. 24 (0.02 millimoles) and 6-(N-succinimidyloxycarbonyl)fluorescein (11.8 mg) were stirred in 0.35 ml of dimethylformamide for 4 hours at ambient temperature. The solvent was removed, and the residue was chromatographed on thin layer silica gel plates with chloroform-methanol and again with benzene-ethyl acetate-acetone to give the pure tracer.

EXAMPLE 7

Preparation of the Tracer of FIG. 12

This compound was prepared according to the method of Example 6 from 0.02 millimoles of the precursor of FIG. 25 and 11.8 mg of 6-(N-succinimidyloxycarbonyl)fluorescein, chromatographing first with benzene-ethyl acetate-hexane and then with chloroform-methanol.

EXAMPLE 8

Preparation of the Tracer of FIG. 13

The precursor of FIG. 25 (0.02 millimoles) and 2-(fluorescein-6-ylamino)-4,6-dichloro-1,3,5-triazine were taken up in 0.40 ml of methanol and stirred at ambient temperature overnight. The product was purified by chromatography on thin layer silica gel developed with chloroform-methanol and with benzene-ethyl acetate-acetone.

EXAMPLE 9

Preparation of the Tracer of FIG. 14

Figure 26:
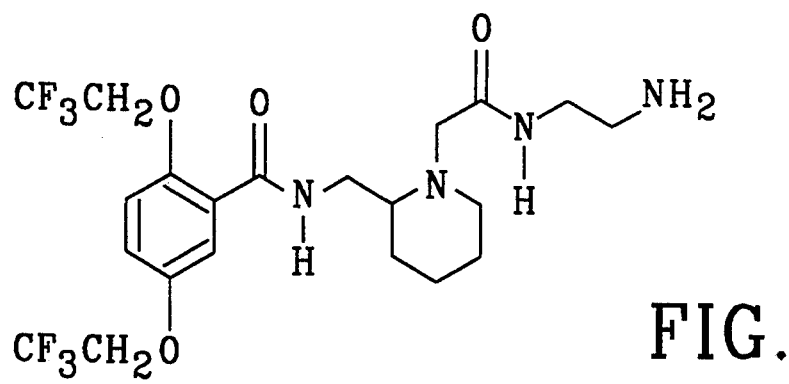

The compound was prepared according to the method of Example 8 from 0.02 millimoles of the precursor of FIG. 26 and 13.3 mg of 2-(fluorescein-5-ylamino)-4,6-dichloro-1,3,5-triazine in 0.20 ml of methanol. Chromatographic purification was with chloroform-methanol.

EXAMPLE 10

Preparation of the Tracer of FIG. 15

This compound was prepared according to the method of Example 6 from 0.02 millimoles of the precursor of FIG. 26 and 11.8 mg of 6-(N-succinimidyloxycarbonyl)fluorescein in 0.25 ml of dimethylformamide.

EXAMPLE 11

Preparation of the Tracer of FIG. 16

Figure 27:
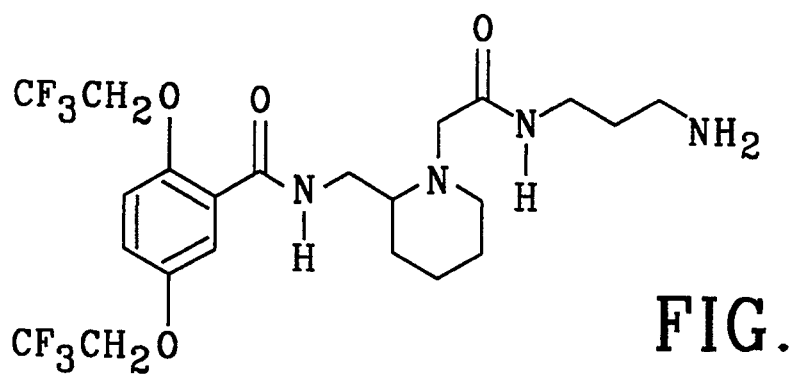

This compound was prepared according to the method of Example 8 from 0.02 millimoles of the precursor of FIG. 27 and 13.3 mg of 2-(fluorescein-6-ylamino)-4,6-dichloro-1,3,5-triazine in 0.20 ml of methanol.

EXAMPLE 12

Preparation of the Tracer of FIG. 17

This compound was prepared according to the method of Example 6 from 0.02 millimoles of the precursor of FIG. 27 and 11.8 mg of 6-(N-succinimidyloxycarbonyl)fluorescein in 0.25 ml of dimethylformamide. Chromatography was with chloroform-methanol.

EXAMPLE 13

Preparation of the Tracer of FIG. 18

Figure 28:
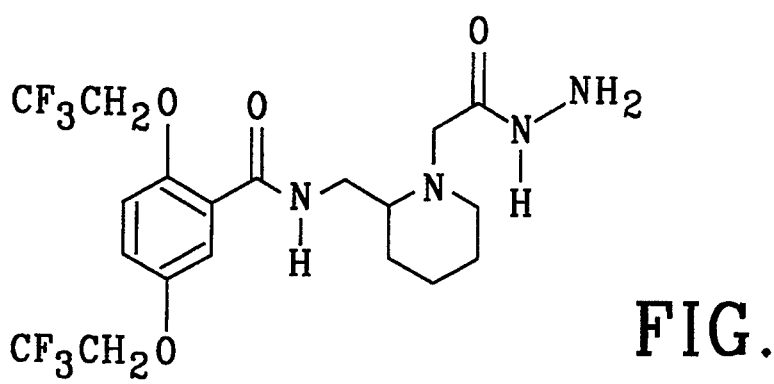

This compound was prepared according to the method of Example 6 from 0.02 millimoles of the precursor of FIG. 28 and 11.8 mg of 6-(N-succinimidyloxycarbonyl)fluorescein in 0.20 ml of dimethylformamide. Chromatography was with chloroform-methanol.

EXAMPLE 14

Preparation of the Tracer of FIG. 19

A mixture of 0.02 millimoles of the precursor of FIG. 27 and 13.2 mg of 2-(fluorescein-5-ylamino)-4-methoxy-6-chloro-1,3,5-triazine in 0.50 ml of methanol was stirred and heated in a 50° oil bath for 6½ hours. The crude reaction mixture was streaked onto a thin-layer silica gel plate and developed with chloroform-methanol to give the pure tracer.

EXAMPLE 15

Preparation of the Tracer of FIG. 20

This compound was prepared according to the method of Example 14 from 0.02 millimoles of the precursor of FIG. 27 and 13.2 mg of 2-(fluorescein-6-ylamino)-4-methoxy-6-chloro-1,3,5-triazine. Chromatography was with chloroform-methanol and benzene-ethyl acetate-acetone.

EXAMPLE 16

Preparation of the Tracer of FIG. 21

A mixture of N-(3-aminopropyl)flecainide (FIG. 29) and 5.3 mg of 2-(fluorescein-6-ylamino)-4,6-dichloro-1,3,5-triazine was stirred at ambient temperature in 0.2 ml of methanol for 24 hours. The product was purified by chromatography on silica gel thin layer plates with chloroform-methanol and benzene-ethyl acetate-acetone.

EXAMPLE 17

Preparation of the Tracer of FIG. 5

This compound was prepared according to the method of Example 16, except that the 5-isomer instead of the 6-isomer of the fluorescent labeling reagent was employed.

EXAMPLE 18

Preparation of the Tracer of FIG. 22

Figure 29:
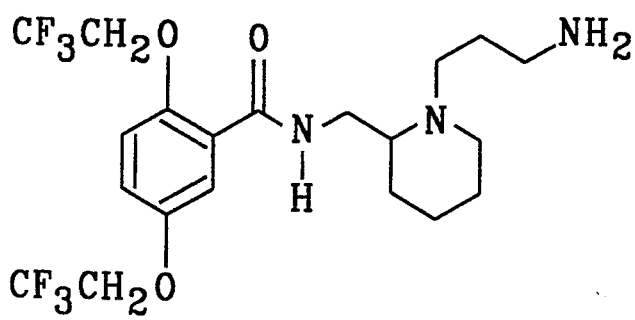

The precursor of FIG. 29 (4.7 mg) and 6-(N-succinimidyloxycarbonyl)fluorescein (4.7 mg) were stirred in 0.20 ml of dimethylformamide for 24 hours at ambient temperature. The solvent was removed, and the residue was chromatographed on a thin layer silica gel plate with chloroform-methanol, followed by a second chromatography on a $C_{18}$-reversed-phase plate developed with water-methanol containing 0.5% acetic acid.

EXAMPLE 19

Preparation of the Tracer of FIG. 23

This compound was prepared by the method of Example 18, except that the 5-isomer of the activated carboxyfluorescein was employed instead of the 6-ksomer. Purification was by chromatography twice on silica gel plates with chloroform-methanol.

What is claimed is:

1. A compound for use in a fluorescence polarization immunoassay, of the structure:

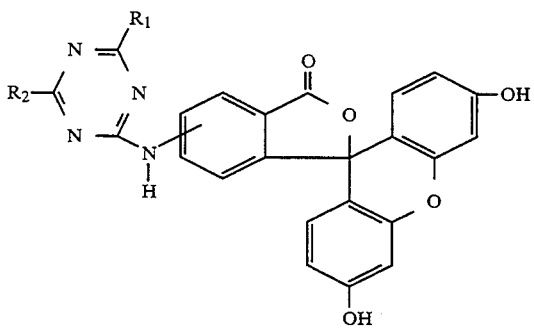

wherein $R_1$ is a halogen;

$R_2$ is —X—$R_3$;

X is selected from —$(CH_2)_3NH$— or

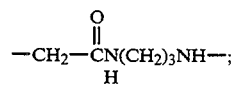

and $R_3$ is

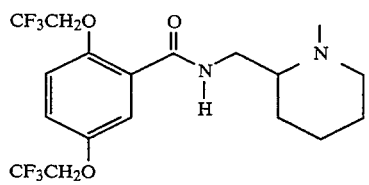

2. The compound according to claim 1 which is:

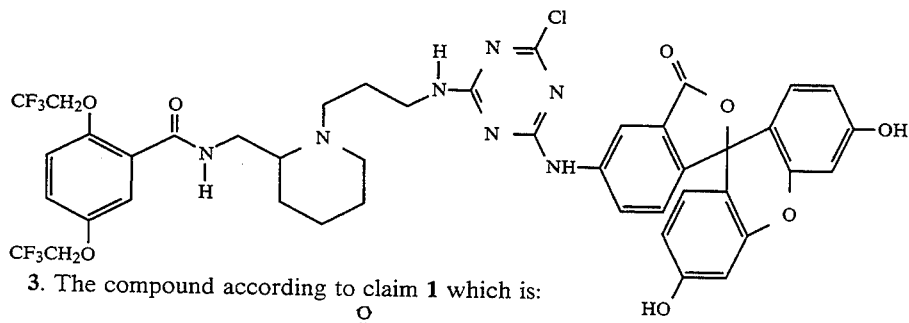

3. The compound according to claim 1 which is:

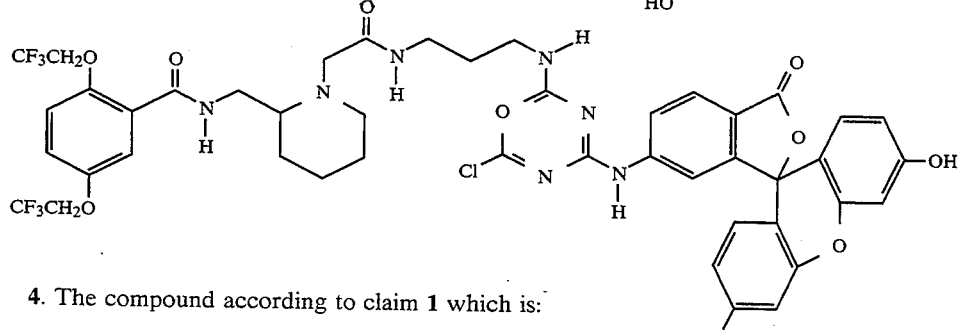

4. The compound according to claim 1 which is:

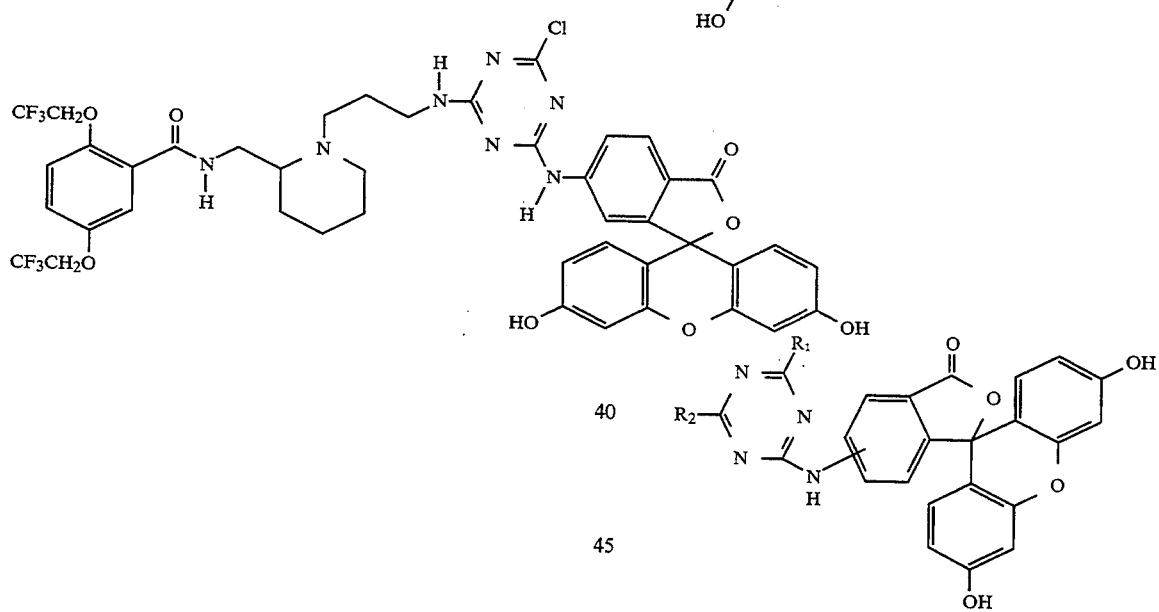

5. A fluorescence polarization immunoassay kit for flecainide, comprising:
   a tracer solution wherein said tracer is a compound of claim 1; and
   antibodies against flecainide capable of recognizing and binding flecainide and said tracer.

6. A method for determining the presence or amount of flecainide in a test sample, comprising the steps of:
   a) contacting the sample with a tracer and an antibody capable of recognizing and binding the analyte and said tracer, whereby binding of (i) said analyte or (ii) said tracer to said antibody blocks binding of (i) said tracer or (ii) said analyte, respectively, to said antibody; wherein said tracer comprises a compound of the formula:

wherein
$R_1$ is a halogen;
$R_2$ is $-X-R_3$;
X is $-(CH_2)_3NH-$ or $-CH_2-C(O)NH(CH_2)_3NH-$; and
$R_3$ is

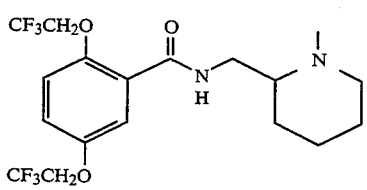

b) passing plane polarized light through said test solution to obtain a fluorescence polarization response; and
c) detecting the fluorescence polarization response as a measure of the presence or amount of flecainide analyte in the test sample.

* * * * *